(12) United States Patent
Bauduin et al.

(10) Patent No.: US 8,410,306 B2
(45) Date of Patent: Apr. 2, 2013

(54) METHOD OF PRODUCING A CARBOXYLIC ALKYL ESTER

(75) Inventors: Christophe Bauduin, Mannheim (DE); Wolfgang Fischer, Lingenfeld (DE); Rolf Pinkos, Bad Dürkheim (DE); Edzard Scholten, Mannheim (DE)

(73) Assignee: BASF SE, Ludwigshafen (DE)

( * ) Notice: Subject to any disclaimer, the term of this patent is extended or adjusted under 35 U.S.C. 154(b) by 448 days.

(21) Appl. No.: 12/295,996

(22) PCT Filed: Apr. 4, 2007

(86) PCT No.: PCT/EP2007/053339
§ 371 (c)(1), (2), (4) Date: Oct. 3, 2008

(87) PCT Pub. No.: WO2007/116005
PCT Pub. Date: Oct. 18, 2007

(65) Prior Publication Data
US 2009/0137825 A1    May 28, 2009

(30) Foreign Application Priority Data
Apr. 4, 2006  (EP) .................................... 06007118

(51) Int. Cl.
C07C 69/40 (2006.01)
C07C 69/66 (2006.01)

(52) U.S. Cl. ........................................ 560/190; 560/180

(58) Field of Classification Search .................. 562/589, 562/580; 560/179, 180, 190
See application file for complete search history.

(56) References Cited

U.S. PATENT DOCUMENTS

| 2,722,541 | A | 11/1955 | Schulz et al. |
| 5,869,301 | A | 2/1999 | Nghiem et al. |
| 6,028,215 | A | 2/2000 | Bessling et al. |
| 6,291,708 | B1 * | 9/2001 | Cockrem ...................... 562/589 |
| 2007/0135650 | A1 | 6/2007 | Rosch et al. |

FOREIGN PATENT DOCUMENTS

| DE | 19829809 A1 | 1/1999 |
| WO | WO-98/23579 A1 | 6/1998 |
| WO | WO-00/64850 A1 | 11/2000 |
| WO | WO-2005/051885 A1 | 6/2005 |
| WO | WO-2005/058853 A2 | 6/2005 |

OTHER PUBLICATIONS

Cheng et al, Effects of feed tray locations to the design of reactive distillation and its implication to control, May 2005, Chemical Engineering Science 60(2005), p. 4661-4677.*
Varadarajan et al., "Catalytic Upgrading of Fermentation-Derived Organic Acids," Biotechnol. Prog., vol. 15, pp. 845-854 (1999).
Olson et al., "Ester Fuels and Chemicals from Biomass," Applied Biochemistry and Biotechnology, vol. 105-108, pp. 843-851 (2003).

* cited by examiner

Primary Examiner — Taylor Victor Oh
(74) Attorney, Agent, or Firm — Novak Druce Connolly Bove + Quigg LLP

(57) ABSTRACT

The present invention relates to a novel process for preparing alkyl polycarboxylates from an aqueous solution of an ammonium salt of the polycarboxylic acid by reactive distillation, and to a process for hydrogenating the alkyl carboxylates prepared in this way.

23 Claims, 3 Drawing Sheets

METHOD OF PRODUCING A CARBOXYLIC ALKYL ESTER

RELATED APPLICATIONS

This application is a national stage application (under 35 U.S.C. §371) of PCT/EP2007/053339, filed Apr. 4, 2007, which claims benefit of European Application No. 06007118.0, filed Apr. 4, 2006.

The present invention relates to a novel process for preparing alkyl polycarboxylates from an aqueous solution of an ammonium salt of the polycarboxylic acid, and to a process for hydrogenating the alkyl carboxylates prepared in this way.

BACKGROUND OF THE INVENTION

Organic carboxylic acids and their esters constitute important starting materials for chemical synthesis. It is of particular economic significance to prepare such organic carboxylic acids and their esters at minimum cost. The fermentative preparation of carboxylic acids using suitable microorganisms is gaining increasing importance. However, a disadvantage in these processes is that the carboxylic acids are usually not obtained as the pure substance and additionally not in the form of the free acid, but rather neutralized partly or fully in salt form. Neutralization is usually necessary, since the fermentation broth would otherwise overacidify with increasing fermentation time and, as a consequence thereof, the microorganism would be damaged. The pure preparation of carboxylic acids or the corresponding esters synthesized fermentatively but also chemically is therefore of great significance.

Starting from carboxylic acids prepared fermentatively, especially lactic acid or succinic acid, a wide variety of different products of value are obtainable by a chemical route with the aid of different synthesis strategies (cf., for example, review article by Varadarajan et al., *Biotechnol. Proc.* 1999, 15, 845-854).

The prior art also describes various strategies for working up carboxylic acids, especially for esterifying carboxylic acids. For example, WO-A-00/64850 addresses the preparation of organic acids from the corresponding ammonium salts by thermal decomposition of an aqueous ammonium salt solution of the organic acid in the presence of an alcohol and removal of a vaporous mixture of ammonia, water and alcohol from the reaction mixture. If desired, the organic acid formed can be converted to an ester. However, the maximum ester yield in this process is obviously very low; for instance, in the working examples there, a maximum yield of only 14.6% is described for ethyl lactate. This process thus appears to be unsuitable for the quantitative conversion of an ammonium salt of an organic acid to the corresponding ester. Furthermore, the usability of the system described there for esterifying polycarboxylic acids is not confirmed by any examples whatsoever. Moreover, the process described there possesses the disadvantage that reaction products with an undesirably high proportion of incorporated nitrogen are obtained. For instance, a content of incorporated nitrogen (lactamide content) of 16.7 mmol is calculated from the nitrogen analyses described therein (example 8 therein) for the product-containing bottoms in spite of two repetitions of the stripping, which, when converted, corresponds to about 18.9% of the nitrogen used (approx. 88 mmol of ammonium lactate).

The esterification of carboxylic salts prepared by fermentation by catalytic reaction of a salt/alcohol mixture and subsequent removal of the ammonia and water formed by pervaporation is described in WO-A-98/23579. However, a disadvantage in this process is the necessity of the use of pervaporation membranes. Furthermore, in the working examples there, esterification rates of not more than 40.7% (in the conversion of ammonium propionate to the corresponding ethyl ester) are described. This process too thus appears to be unsuitable for a highly quantitative esterification of ammonium salts of carboxylic acids. Furthermore, the usability of the system described there for esterifying polycarboxylic acids is not confirmed by any examples whatsoever.

The single-stage or multistage esterification of free mono-, di- or polycarboxylic acids by reacting a carboxylic acid/ alcohol mixture in a reactor is described in WO-A-20051051885. However, there is no indication of the usability of this process for the esterification of corresponding ammonium salts.

The provision of ester-containing fuels and chemicals from biomass by reacting biologically prepared alcohols, especially methanol and ethanol, and carboxylic acids prepared by fermentation, especially their ammonium salts, is proposed by Olson et al. in *Applied Biochemistry and Biotechnology*, 2003, Vol. 105-108, 843-851. Various methods for preparing monocarboxylic esters are discussed. The successful esterification of polycarboxylic salts is not described in this document.

DE-A-198 29 809 describes the esterification of a mixture of water and free monocarboxylic acid by reactive distillation.

In addition, none of the documents cited addresses the controlled avoidance of undesired nitrogen-containing byproducts of the esterification reaction, especially of chemically stable carboximides, whose formation in the esterification of ammonium carboxylates constitutes a significant problem. In addition, such imides can be removed from the reaction mixture only with difficulty and can have a disruptive effect in later chemical reactions.

It is therefore an object of the present invention to provide an improved process for preparing polycarboxylic esters from the corresponding ammonium salts, which firstly ensure a high ester yield and secondly largely prevent the formation of undesired nitrogen-containing by-products, especially of carboximides.

SUMMARY OF THE INVENTION

Figure 1:
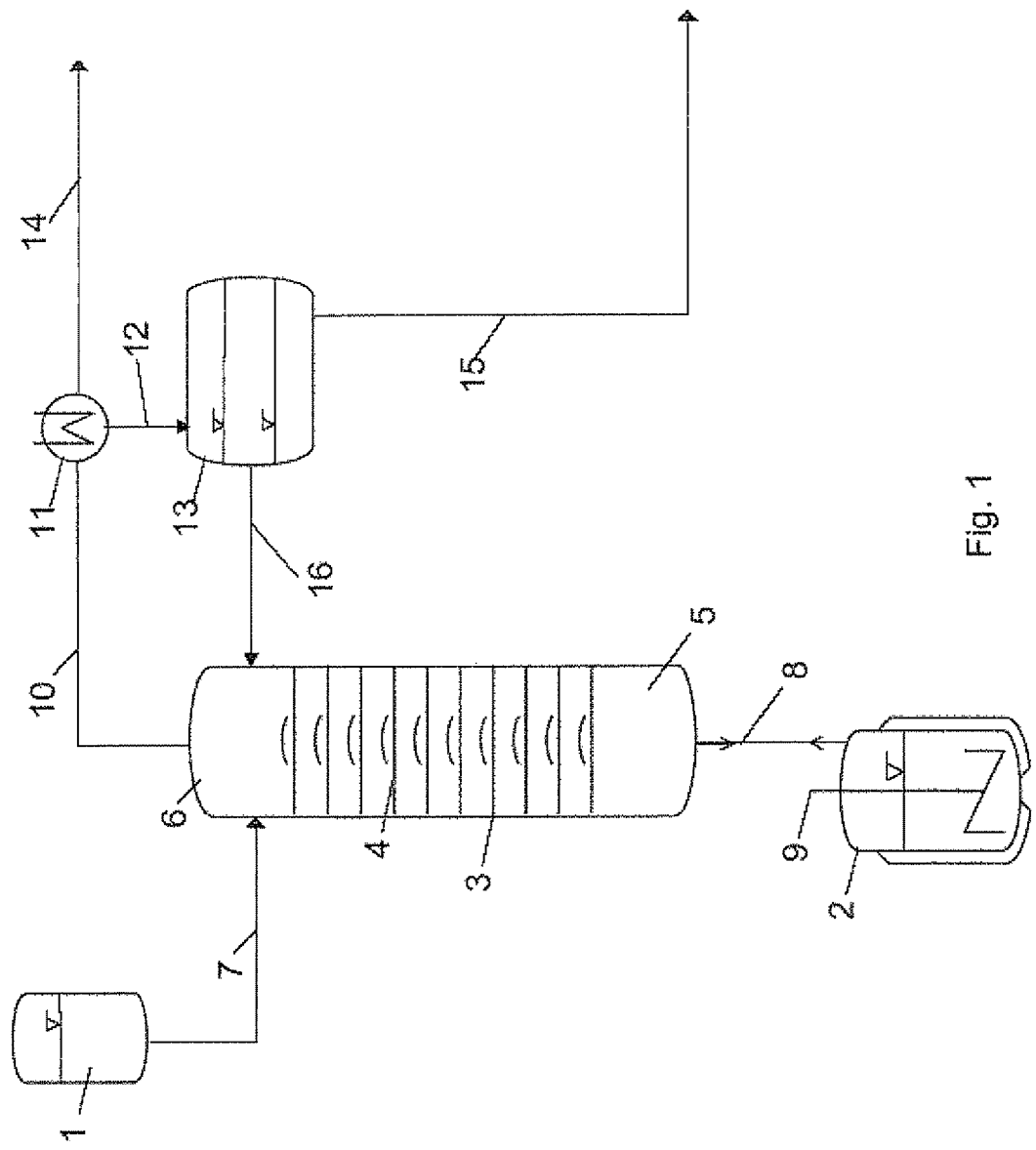
FIG. 1 shows, in schematic illustration, an example of an apparatus for performing the inventive esterification by reactive distillation in a bubble-cap tray column which is operated in semibatchwise mode.

The above object is surprisingly achieved by providing a process for preparing a polycarboxylic ester, in which a reactive distillation is carried out by contacting an initial charge comprising an aqueous solution of an ammonium salt of the polycarboxylic acid with alkanol in a distillation column and removing ammonia and water obtained in the esterification from the reaction by distillation.

When the inventive teaching is followed, it is surprisingly possible to provide the desired polycarboxylic ester in significantly improved yield and surprisingly high purity. For instance, esterification yields of 80 to 100%, for example from 90 to 99% or from 92 to 98%, based on the amount of carboxylic acid used, can be achieved.

In particular, the content and undesired nitrogen compounds in the product can additionally be reduced significantly, so that direct catalytic hydrogenation of the ester is enabled. It has thus been possible in accordance with the invention for the first time to provide esterification products which have a surprisingly low residual content of undesired nitrogen compounds. Thus, nitrogen incorporation rates of less than 1%, especially less than 0.5%, for example less than 0.1%, have been achieved.

DETAILED DESCRIPTION OF THE INVENTION

1. Preferred Embodiments of the Invention

The invention firstly relates to a process for preparing at least one alkyl carboxylate, especially polycarboxylic ester, for example a dialkyl dicarboxylate wherein a reactive distillation is carried out by contacting an initial charge comprising an aqueous solution of an ammonium salt of the carboxylic acid, which especially comprises essentially no alkanol capable of ester formation and is preferably alkanol-free in at least one distillation column, especially one or two distillation columns connected together in a manner known per se, with alkanol, for example in cocurrent or especially in countercurrent, and removing ammonia and water obtained in the esterification from the reaction by distillation, the carboxylic ester formed or its precursors (for example, in the case of dibutyl succinate, the monoester and succinic anhydride) becoming enriched, for example in the bottom of the column, or passed from their out of the column. If required, one or more delay vessels may be provided in a manner known per se on one or more and/or between two or more distillation columns, in order to improve conversion, for example to achieve full conversion. According to the invention, the carboxylic salt (for example in the form of optionally heated liquid) and alkanol (for example in vapor form or in the form of optionally heated liquid) reactants are contacted "in the distillation column" by introducing them into the reaction chamber especially in reactant streams spatially separate from one another. In contrast to the prior art discussed above, introduction of alkanol and carboxylic salt together, i.e. in a mixture, into the reaction chamber is thus avoided from the outset. In particular, the two reactants are fed in separately from one another such that the residence time of ammonia released in the reaction zone of the column is greatly reduced, in particular is as short as possible, and hence the probability of formation of undesired nitrogen-containing by-products, such as of amido esters or dicarboximides, is kept at a minimum. This is a significant problem especially when, as in the case of the present invention, a relatively large amount of nitrogen is introduced (owing to the polycarboxylic acid reactant present in ammonium salt form).

The ammonium polycarboxylate content of the initial charge is commonly in the range from about 1 to 60 or from 10 to 50 or from 30 to 45% by weight, based on the total weight of the initial charge. The water content should of course be as low as possible, but it should, on the other hand, be high enough to keep the carboxylic salts in solution.

The process according to the invention can be carried out in different modes, such as in batch mode, semibatch mode or continuously.

Especially in the case of continuous mode, it is advantageous to recycle reusable by-products of the reaction, for example ammonia or unconverted alcohol or alcohol which is released in a later reaction step, back into the process at a suitable point. Ammonia can, for example, be reused to neutralize the polycarboxylic acid.

The salt of a carboxylic acid used in accordance with the invention is preferably selected from aliphatic $C_3$-$C_{20}$-polycarboxylic acids, saturated or unsaturated in each case, i.e. carboxylic acids having two or more, for example 2, 3 or 4 carboxyl groups, especially dicarboxylic acids, preferably saturated dicarboxylic acids, and mixtures thereof. The polycarboxylic acid has been neutralized partly or fully by ammonia. The ammonium carboxylate used is more preferably diammonium succinate.

According to the invention, the terms "alkanol" and "alcohol" are used synonymously. In particular, moreover, an alkanol (if appropriate in concentrated, pure form, for example in anhydrous form) which is selected from straight-chain or branched $C_1$-$C_8$-monoalkanols, especially straight-chain or branched $C_3$-$C_6$-monoalkanols, is used for the esterification. In a preferred variant, the alkanol used is n-butanol and the esterification product obtained is di-n-butyl succinate.

In a further embodiment of the invention, the reaction is carried out in the presence of an esterification catalyst.

In a preferred configuration of the process according to the invention, the aqueous polycarboxylic salt-containing, especially alkanol-free or essentially alcohol-free, solution (i.e. comprising only traces of alkanol, for example less than 5% by volume, such as from 0 to 2% by volume, from 0 to 1% by volume, from 0 to 0.1% by volume or from 0.001 to 0.05% by volume) and the alkanol are fed to the distillation column in at least two spatially separate reactant streams. "Spatially separate" may mean "at the same height" or "offset relative to one another in terms of height"; for example, for a given feed point for the carboxylic salt solution, the alkanol can be fed in above it (i.e. further in the direction of the top of the column) or below it (i.e. further in the direction of the lower end of the column).

In addition to the surprisingly reduced formation of undesired nitrogen by-products, this has the further advantage over the prior art that the demixing problem which otherwise occurs when aqueous solutions of higher alkanols with carboxylic salts, for example butanol, are used does not exist and a more homogeneous process regime is enabled in accordance with the invention.

The exact selection of the feed point for the alcohol is variable according to the alcohol used. The lower the boiling point of the alkanol, the lower the feed will be arranged in the column, such that, in this way, the contact time between the reactants can be set optimally. This is possible for the person skilled in the art with the aid of a few preliminary tests.

For example, it is possible in accordance with the invention to prepare carboxylic esters in quantitative or approximately quantitative yield (for example more than 90%, or more than 95, 96, 97, 98 or 99%), in which case the reaction mixtures obtained, without further purification steps, have contents of incorporated nitrogen in the ppm range, for example from 0 to 500 ppm or from 10 to 200 ppm or from 20 to 100 ppm. In addition, the process according to the invention can achieve nitrogen incorporation rates (i.e. nitrogen contents for nitrogen in bound form) of less than 1 mol %, especially less than 0.5 mol %, for example less than 0.1 mol %, based on the ammonium salt nitrogen used.

More particularly, preference is given to feeding in the aqueous carboxylic salt-containing solution in the upper half of the distillation column, for example below the top of the column, or at the level of the condenser reflux. This promotes rapid ammonia discharge. The alkanol is fed in at a distance from this, via a feed offset in the direction of the upper end of the column or especially of the lower end of the column, for example via the column bottom itself.

More particularly, the alkanol can be added to the distillation column at least one theoretical plate, for example from 2 to 20 or from 5 to 10 theoretical plates, or at least one tray, for example from 2 to 20 or from 5 to 10 trays, above or especially below the feed of the aqueous carboxylic salt-containing solution.

Moreover, it is not absolutely necessary in accordance with the invention to perform the reactive distillation with supply of inert gas (for example nitrogen supply), since the above-described configuration of the separate reactant supply already enables very efficient ammonia removal with simultaneous prevention of by-product formation.

Overall, the person skilled in the art, while following the inventive general teaching, can configure (i.e. adjust and keep constant or vary during the reaction) the reaction conditions, such as residence time, reactor temperature, if appropriate pressure, feed rate and/or molar ratio of the reactants, discharge rate of water/ammonia, so as to achieve a desirably high, substantially quantitative ester yield with low nitrogen incorporation. Pressure and/or temperature can, if appropriate, also be adjusted such that the formation of alkanol vapor further improves the discharge of ammonia.

The ammonia and water released in the reaction (if appropriate together with small amounts of alkanol) can be distilled off via the top of the column, in which case an alkanol/water mixture or azeotrope (depending on the alkanol used) and ammonia is distilled off and condensed, and the alkanol is obtained from the condensate and recycled into the reaction separately from the carboxylic salt feed (i.e. at the same level or offset therefrom), or an alkanol/water heteroazeotrope and ammonia are distilled off and condensed, and the organic alkanol phase is removed from the condensate (for example by phase separation or by distillation) and recycled into the reaction separately from the carboxylic salt feed (i.e. at the same level or offset therefrom). Azeotropic mixtures can be formed especially in the case of use of ethanol, propanol and butanol; hetreoazeotropes in the case of use of butanol, pentanol and higher alcohols.

When more volatile components than the alcohol-containing azeotrope or alcohol-water mixture to be removed are obtained in the reactive distillation, this more volatile component can be drawn off via the top together with ammonia, and the alcohol-containing mixture or azeotrope can be drawn off at the side below the top of the column.

A preferred process variant comprises the use of a homogeneous or a heterogeneous esterification catalyst, the heterogeneous catalyst being in particular an acidic ion exchange catalyst and the heterogeneous catalyst being fixed on or in column internals.

In a preferred embodiment, a homogeneous catalyst, for example p-toluenesulfonic acid, is used, which is added to the aqueous ammonium salt solution of the carboxylic acid.

The ammonium carboxylate used in the esterification process according to the invention may either be prepared chemically or be a fermentation broth which has been prepurified and/or concentrated if appropriate and comprises one or more ammonium carboxylates. The fermentation broth may also comprise free acid or partly neutralized salts and, for the reaction, it may be partly or fully neutralized by adding ammonium ions, for example by adding ammonium hydroxide or ammonium carbonate. Suitable fermentation broths stem, for example, from the cultivation of a microorganism which ferments pentoses and/or hexoses, and/or polyols, especially glucose and/or glycerol.

The invention further relates to a process for hydrogenating alkyl polycarboxylates, wherein an esterification reaction as defined above is first carried out, the alkyl polycarboxylate, for example monoalkyl and especially dialkyl succinates, is purified if appropriate from the ester-containing reaction mixture obtained, for example by means of distillation, the ester is hydrogenated catalytically and the desired product of value is isolated, for example purified by distillation. For the hydrogenation, preference is given to using a supported CuO catalyst.

Particular preference is given to hydrogenating dialkyl succinate, especially di-n-butyl succinate, to tetrahydrofuran, 1,4-butanediol, gamma-butyrolactone or mixtures of these compounds.

2. Further Embodiments of the Invention a) Reactive Distillation of the Ester According to the invention, a "reactive distillation" is understood to mean the simultaneous performance of a chemical reaction and of a distillation or rectification. This simultaneous performance of reaction and separation is particularly advantageous in those reactions in which, owing to the position of the chemical equilibrium, the reactants are not fully converted to the desired products. As a result of the simultaneous removal of the reaction products from the reaction chamber, an almost full conversion is achieved in a single apparatus. Further advantages of reactive distillation are the suppression of undesired side reactions, the thermal utilization of exothermic heat of reaction for the distillation and the facilitation of the subsequent product workup.

The apparatus of the inventive reactive distillation can be designed in various configurations. In principle, suitable designs for this purpose are all known designs of distillation or rectification columns and all types of reactors in which simultaneous distillation is possible.

A "rectification column" consists conventionally of an evaporator at the bottom, a condenser at the top and various internals in the column. Depending on the type of internals used, a distinction is drawn between tray columns, columns with random packing and columns with structured packing. The substance to be separated is fed in through a feed. The relatively low-boiling components accumulate in the top and can be removed there. In order to achieve the separation in the column, a substream of the condensate is conventionally returned back into the column. The relatively high-boiling components accumulate in the bottom and can be removed there. The possibility additionally exists, depending on the separation problem, of obtaining components which are between the lowest- and the highest-boiling components through a side draw.

Sieve trays, bubble-cap trays or valve trays through which the liquid flows are incorporated into typical tray columns. The vapor is passed through special slots or holes, so as to form a froth layer. A new evaporation equilibrium is established on each of these trays.

Columns can be filled with differently shaped random packings. The associated increase in the surface area of the random packings which are about 3-50 mm in size optimizes heat and mass transfer and hence increases the separation capacity of the column. Typical examples of such substrates are the Raschig ring (a hollow cylinder), Pall ring, Hiflow ring, Intalox saddle, Berl saddle and Igel [hedgehog]. The random packings may be introduced into the column in an ordered manner, but also randomly (as a bed). Useful materials include glass, ceramic, metal and plastics.

Structured packings are a further development of the ordered random packings. They have a regularly shaped structure. There are various designs of structured packings, for example fabric or sheet metal packings. The material used may be metal, plastic, glass and ceramic. In comparison to tray columns, columns with structured packing have very low liquid contents. This is often advantageous for the rectification, since this reduces the risk of thermal decomposition of the substances.

For the reactive distillation, the low liquid contents of columns with structured packing is not always appropriate, especially in the case of reactions with finite reaction rate. In order to achieve the desired conversion in slow reactions, a high residence time of the liquid in the apparatus should be ensured. For this purpose, it can often be helpful to connect one or more external vessels in which a majority of the actual reaction takes place alongside or downstream of the column, especially alongside the column with structured packing.

For the inventive performance of the reactive distillation, the use of tray columns is a particularly suitable variant. Tray columns have high liquid contents, both in the biphasic layer on the tray and in the downcomers. The two fractions of the liquid contents can be changed in a controlled manner by construction measures, for example by the configuration of the trays, and adjusted to the particular requirements of the reactive distillation. The design of optimal internals for a reactive tray column optimized in accordance with the invention is within the ability of the person skilled in the art. In particular, a person skilled in the art can take suitable construction measures to realized suitable liquid contents and hence suitable residence times, and also for the filling with heterogeneous catalyst if required.

A high level of liquid contents in the biphasic layer on the trays can be established in the simplest manner by the use of high overflow weirs. A disadvantage may be here a high pressure drop of the vapor and the large construction height of the column required. It appears to be more advantageous to realize a high level of liquid contents in the downcomers, since no additional pressure drop arises in this case. In this case, reaction and distillation can proceed largely separately on each tray, specifically the reaction in the downcomer and the distillation in the biphasic layer on the tray. A further conceivable modification would be the use of an alternating sequence of exchange trays and chimney or reaction trays with a high level of liquid content.

b) Suitable Reactants and Esterification Catalysts

Polycarboxylic acids esterifiable in accordance with the invention have 2 or more, especially 2, 3 or 4, preferably 2 carboxyl groups. In particular, these are straight-chain or branched, aliphatic or cycloaliphatic, saturated or unsaturated polycarboxylic acids having from 2 to 20, for example from 2 to 10 or from 3 to 8, in particular 4, 5 or 6 carbon atoms which are optionally substituted by one or more hydroxyl groups. Specific examples include dicarboxylic acids such as oxalic acid, maleic acid, itaconic acid, fumaric acid, succinic acid, methylsuccinic acid, glutaric acid, 2- or 3-methylglutaric acid, adipic acid and their hydroxy-substituted derivatives, for example maleic acid or 2-hydroxyglutaric acid, or mixtures thereof.

Examples of higher polybasic polycarboxylic acids include citric acid, agaricic acid, propane-1,2,3-tricarboxylic acid (tricarballylic acid), aconitic acid or mixtures thereof.

Alkanols useable in accordance with the invention include monools. Particularly useful are $C_1$-$C_{12}$-, $C_1$-$C_{10}$-, $C_1$-$C_8$- or $C_3$-$C_6$-alkanols. Examples include monools whose alkyl moiety is selected from methyl, ethyl, n-propyl, isopropyl, n-butyl, sec-butyl, isobutyl, tert-butyl, pentyl, hexyl, heptyl, octyl, 2-ethylhexyl, nonyl, decyl, undecyl or dodecyl, and the accompanying positional isomers.

The molar ratio of carboxylic acid or salts to alkanol is commonly in the range from 1:1 to 1:10, for example from 1:1 to 1:5 or from 1:1 to 1:2.

Examples of suitable solid esterification catalysts are ion exchange resins obtainable under the trade names Amberlyst 15 or Amberlyst 16 (Rohm and Haas) or DPT1 (Davy Process Technology Limited).

Suitable liquid esterification catalysts are sulfuric acid, p-toluenesulfonic acid, methanesulfonic acid, 4-dimethylaminopyridines (DMAP), or mixtures of tertiary $C_8$-$C_{10}$-amines obtainable under the trade name Alamine 336 (from Henkel)

c) Esterification Processes

The inventive esterification process which comprises essentially a reactive distillation can be performed using an apparatus known per se in various designs. Two nonlimiting, specific examples of inventive procedures are illustrated in detail below with reference to the accompanying figures.

FIG. 1 illustrates an example of an esterification plant which is operated in semibatchwise mode and comprises a bubble-cap tray column 3 with a multitude of bubble-cap trays 4. The aqueous initial charge comprising the ammonium salt of the polycarboxylic acid is fed into the top of the column 6 from the reservoir vessel 1 via the line 7 as soon as a steady-state temperature profile has formed in the column 3 as a result of feeding-in of vaporous alkanol. The initial alcohol charge is present in the heated stirred vessel 2 which is provided with a stirrer 9 and is connected via the connecting line 8 to the lower end 5 of the column 3. The reaction forms a countercurrent flow of descending, ammonium salt-containing liquid and condensate, and ascending, alkanol-containing vapor phase. To catalyze the esterification reaction, a homogeneous catalyst may be added to the ammonium salt initial charge 1. Alternatively, heterogeneous catalysts may be provided in the column internals, for example in the trays 4. The carboxylic ester formed is liquid under the process conditions and passes via the lower end of the column 5 and the connecting line 8 into the stirred vessel 2 which thus simultaneously forms the bottom of the distillation column 3. Gaseous components, for example azeotropic mixtures comprising alkanol-water and/or ammonia, are removed from the reaction column 3 and hence from the reaction equilibrium via the vapor line 10 mounted at the top of the column 6. Passing through the condenser 11 liquefies liquefiable fractions of the discharged phase, and they are conducted into the phase separation vessel 13 via the outlet 12. Unliquefiable fractions, especially ammonia, are removed via the offgas line 14. In the phase separation vessel 13, the condensate is separated into organic and aqueous phase. The aqueous phase comprising essentially water is discharged via the outlet 15. The alkanol-containing organic phase is recycled via the line 16 into the top of the column 6 and hence into the process.

Figure 2:
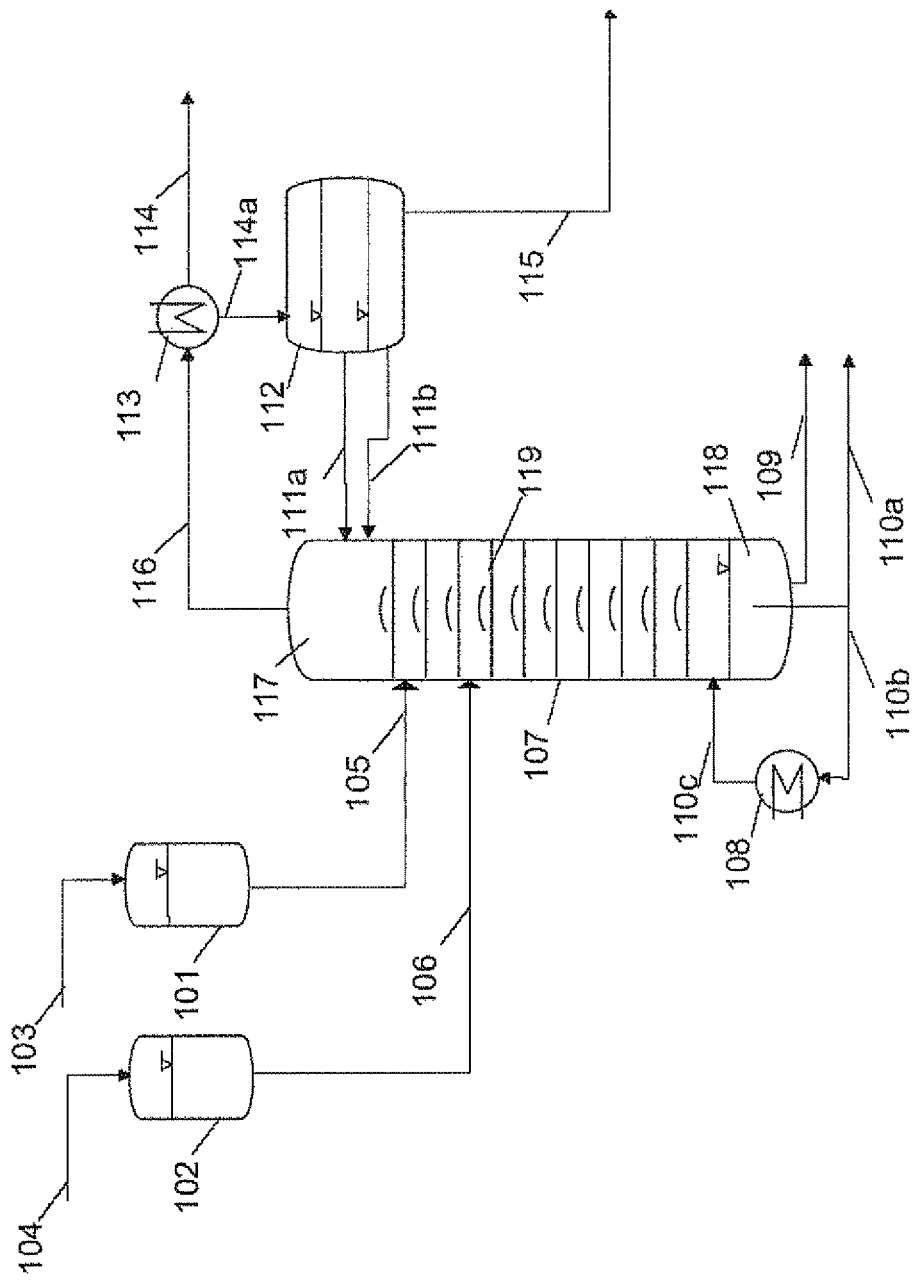
FIG. 2 shows, in schematic illustration, a further example of an apparatus for performing the inventive esterification by reactive distillation in a column with internals; here, for example, a bubble-cap tray column which is operated in continuous mode.
Figure 3:
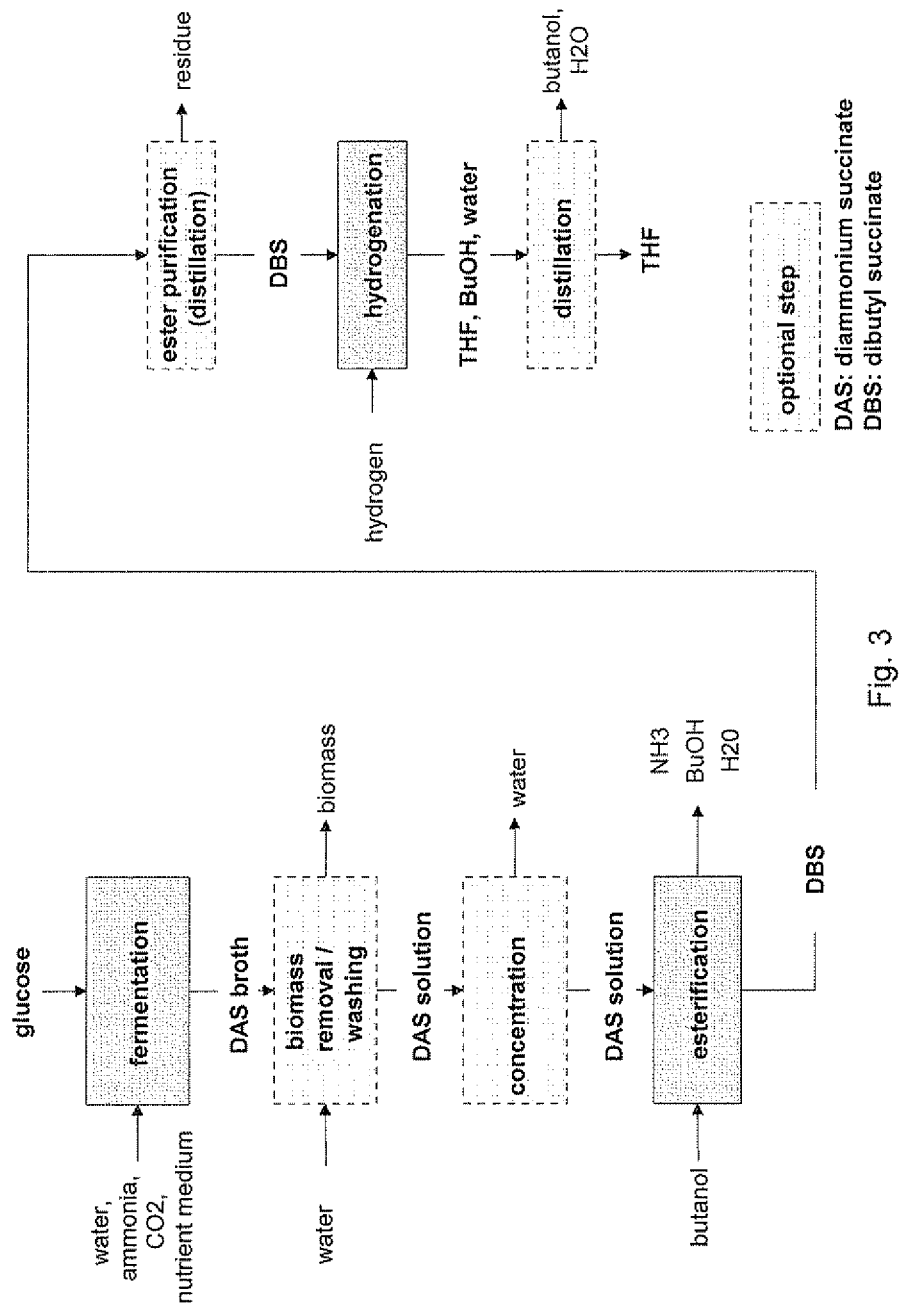
FIG. 3 shows the flow diagram of an inventive overall process for preparing tetrahydrofuran, starting from a fermentation with glucose as the substrate via the esterification of the resulting diammonium salt of succinic acid (DAS) with butanol to give dibutyl succinate (DBS) and the catalytic hydrogenation of the ester to give tetrahydrofuran (THF). Optional process steps are emphasized by broken borders. Possible modifications and supplementations to this overall process, for example the recycling of butanol released and/or the recycling of ammonia released, are not specified for reasons of clarity.

FIG. 2 shows an example of a continuous distillation plant which again comprises a bubble-cap tray column 107 with a multitude of bubble-cap trays 119. The apparatus further comprises reservoir vessels 101 and 102 for the aqueous ammonium polycarboxylate solution and for the alcohol respectively. Ammonium salt solution, if appropriate in a mixture with homogeneous catalyst, from a precursor, for example the fermentative preparation of an ammonium salt-containing fermentation broth, is fed in continuously via the inlet 103. Pure alcohol or alcohol from the recycle stream of the continuous process is fed continuously into the reservoir vessel 102 via the inlet 104. Butanol is fed into the reactive column 107 via the line 106 and passes via the bottom 118 of the column and recycle stream 110b into the evaporator 108, and passes into the column as vapor via the inlet 110. As soon as a steady-state temperature profile has formed, ammonium salt solution is fed into the upper part (top of the column) 117 of the column from the reservoir vessel 101 via the inlet 105. A countercurrent flow of liquid and condensate comprising unesterified carboxylic acid, and ascending alcohol-containing vapor phase forms. Polycarboxylic esters or precursors which are formed during the reaction and are liquid under the process conditions collect in the bottom 118 of the column 107. Gaseous components, especially azeotropic mixtures comprising alcohol, water and/or ammonia, are passed via the top of the column 117 and the outlet 116 out of the column 107 into the condenser 113 and separated there into gaseous and liquid components. Unliquefiable constituents are discharged via the offgas line 114. Liquid constituents pass via the outlet 114a into the phase separation vessel 112. After phase separation, the organic phase is recycled into the top of the column 117 via the recycle line 111a, and the aqueous phase is drawn off via the outlet 115. Optionally, a portion of the aqueous phase in particular can also be recycled into the column 107 via a line 111b. The ester-containing liquid phase which collects in the bottom 118 of the column is removed continuously from the column via line 110a. Optionally, residue formed or collected in the base of the bottom 118 can also be drawn off via a suit 109. Instead of a homogeneous catalyst, a heterogeneous catalyst may also be used in the column 107, which is provided in the region of the column internals 119. Recycling of worked-up alcohol, for example from the water phase, into the alcohol reservoir 102 via the line 104 is possible.

Further modifications of the above-described specific embodiments of apparatus usable in accordance with the invention are conceivable in principle and can be implemented by the person skilled in the art without unacceptable effort.

Suitable process parameter ranges for the esterification process according to the invention can be determined easily by the person skilled in the art depending on the configuration of the apparatus used, for example type of column internals used, type and amount of the reactants, type and amount of the catalyst used if appropriate. For instance, without being restrictive thereto and independently of one another, individual parameters may be set within the following parameter ranges:

Column temperature: 0-300° C., in particular 40-250° C., or 70-200° C.
Pressure: from 0.1 to 6 bar, in particular standard pressure
Residence time: a few seconds (for example from 1 to 60) up to days (for example from 1 to 5), in particular from a few minutes (for example from 1 to 60) to a few hours (for example from 1 to 15), more preferably from a few minutes (for example from 5 to 20) to 2 h.

d) Hydrogenation Process

The polycarboxylic esters prepared in accordance with the invention are hydrogenated in a manner known per se using processes, apparatus and assistants, such as catalysts, familiar to the person skilled in the art.

In particular, a continuous or batchwise gas phase hydrogenation is carried out in the presence of a heterogeneous catalyst suitable for the ester hydrogenation. The optimal process parameters can be established by the person skilled in the art for the particular ester without unacceptable effort. For example, the reaction temperature is in the range from about 100 to about 300° C., preferably in the range from about 200 to 280° C., and the pressure is from about 5 to 100 bar, for example from 10 to 50 bar. The molar ratio of reactant to hydrogen is set within the range from about 1:100 to about 1:2000, for example from 1:800 to 1:1500.

Catalysts usable for the inventive hydrogenation reaction are known to the person skilled in the art. For example, various copper catalysts may be used. The prior art describes, for example, the use of reduced copper chromite catalysts which are obtainable under the name 85/1 from Davy Process Technology Ltd., England. However, catalysts particularly suitable in accordance with the invention are supported copper oxide catalysts, the copper oxide being applied to alumina or silica support materials. The examples of the hydrogenation of succinic esters to BDO/GBL/THF with copper catalysts are also described in the following thesis: Schlander, January, February 2000, University of Karlsruhe, "Gasphasenhydrierung von Maleinsäuredimethylester zu 1,4-Butandiol, gamma-Butyrolacton und Tetrahydrofuran an Kupfer-Katalysatoren" [Gas phase hydrogenation of dimethyl maleate to 1,4-butanediol, gamma-butyrolactone and tetrahydrofuran over copper catalysts].

e) Fermentative Preparation of Ammonium Carboxylates

The fermentative preparation of aqueous ammonium salt solutions of polycarboxylic acids is known per se from the prior art. For example, the U.S. Pat. No. 5,869,301 describes the fermentative preparation of carboxylic acids, especially succinate, from glucose using various microorganisms, especially bacteria of the *Escherichia* genus.

The examples of suitable natural or recombinant, pro- or eukaryotic microorganisms include those which are suitable, under aerobic or anaerobic conditions, for the fermentative production of the desired polycarboxylic acid. Particular mention should be made of bacteria, such as those of the *Escherichia, Bacteroides, Anaerobiospirillum, Actinobacillus* and *Mannheimia* genera, and fungi of the *Rhizopus* and *Aspergillus* genera.

Suitable fermentation conditions, media, fermenters and the like can be determined by the person skilled in the art on the basis of his or her general technical knowledge. To this end, he or she can, for example, make use of the remarks in suitable technical literature, for example Rehm et al., Biotechnology, Vol. 3 Bioprocessing, 2nd Ed., (Verlag Chemie, Weinheim).

To this end, a sterile culture medium is prepared, which comprises the substrate and further additives which may be required for the growth of the microorganism and for product formation, such as carbon and/or nitrogen sources, trace elements and the like, and is inoculated with a suitable amount of a fresh preculture of the microorganism. The cultivation is effected in a suitable fermenter, continuously or batchwise, in the course of which the polycarboxylic acid (or salts thereof) becomes enriched in the medium. During the fermentation, the pH of the fermentation medium is set by adding ammonium-containing solutions, for example ammonium hydroxide or ammonium carbonate, so as to prevent inhibition of the culture. However, it is also conceivable in principle to introduce ammonia or to use ammonium hydrogencarbonate solution. Once fermentation has ended, the fermentation broth which comprises the ammonium salt of the polycarboxylic acid, preferably in dissolved form, can be supplied directly to the inventive esterification reaction. However, preference is given to first removing biomass, for example by centrifugation or filtration. If appropriate, after the washing of the removed biomass and combination of the wash liquid with the ammonium salt solution, the salt concentration, if it is too low, can be increased further, for example by distillative removal of water, so as to form a concentrated aqueous ammonium salt-containing phase which has a percentage content of the salt of the polycarboxylic acid in the range of from about 10 to 70% by weight, preferably from 30 to 50% by weight. This aqueous concentrate is then supplied to the esterification reaction.

In one embodiment of the process according to the invention, the fermentation broth is prepared by anaerobic or aerobic fermentation or a combination of aerobic and anaerobic fermentation, preferably by the fermentation of carbon sources, for example $CO_2$, oils or alcohols, especially glycerol, ethanol, methanol or sorbitol, or sugars, for example $C_6$ or $C_5$ sugars, especially glucose, sorbose, arabinose, xylose or sucrose, in pure form or, for example, as molasses or mixtures of the substances mentioned or their precursors, for example starch, for example together with enzymes, or other possible carbonaceous compositions, for example cellulose, for example in the form of used paper, wood wastes or constituents of starch-containing plants.

For the fermentation, for example, prokaryotic or eukaryotic microorganisms are used, for example bacteria such as *E. coli, Anaerobiospirillum succiniproducens, Actinobacillus succinogenes, Mannheimia succiniproducens* or other bacteria or fungi which produce the desired carboxylic acid, for example succinic acid.

In one embodiment, in the fermentation, a microorganism, for example *E. coli*, is transferred to anaerobic conditions after an aerobic growth phase for the development of biomass. In this anaerobic phase, the synthesis of succinate takes place. Both cultivation steps can take place in particular in complex medium. In a further embodiment, in the fermentation, the cultivation of the microorganism, especially of *E. coli*, proceeds in the anaerobic phase with minimal medium. A further embodiment comprises the repeated recycling of the cells and performance of the anaerobic production phase in complex or minimal medium.

The fermentation can be performed in stirred fermenters, bubble columns and loop reactors. A comprehensive overview of the possible method types including stirrer types and geometric designs can be found in "Chmiel: Bioprozesstechnik: Einführung in die Bioverfahrenstechnik, Band 1" [Bioprocess Technology: Introduction To Bioprocess Technology, Volume 1]. In the process, typical variants available are the following variants known to those skilled in the art or explained, for example, in "Chmiel, Hammes and Bailey: Biochemical Engineering", such as batch, fed batch, repeated fed batch or else continuous fermentation with and without recycling of the biomass. Depending on the production strain, sparging with air, oxygen, carbon dioxide, hydrogen, nitrogen or appropriate gas mixtures can/must be effected in order to achieve good yields.

Before the conversion in the fermentation broth in the process according to the invention, the fermentation broth can be pretreated; for example, the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value. In one embodiment, the fermentation broth can be sterilized or pasteurized.

In a further embodiment, the fermentation broth is concentrated. Depending on the requirement, this concentration can be done batchwise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

In apparatus terms, stirred tanks, falling-film evaporators, thin-film evaporators, forced-flash circulation evaporators and other evaporator types can be utilized in natural or forced circulation mode.

Consequently, the term "fermentation broth" is understood to mean an aqueous solution which is based on a fermentative process and has not been worked up or has been worked up, for example, as described herein.

EXPERIMENTAL SECTION

General Remarks

Analysis of the Acids/Esters/Hydrogenation Products by GC:
Column used: CP-SIL 19CB, 25 m, 0.32 mm, 1.2 μm;
Injector: 235° C.;
FID: 300° C.

Example 1

Preparation of Dibutyl Succinate by Means of Reactive Distillation in a Bubble-Cap Tray Column (Feeding of Vaporous Butanol into the Column Tray)

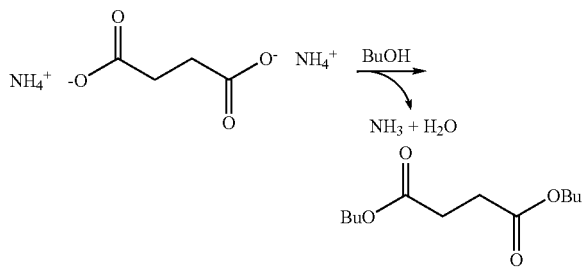

For the esterification reaction, a bubble-cap tray column (insulated by evacuated jacket) (diameter: 0.054 m, number of trays: 10) is used, whose bottom is connected to a heated stirred vessel (size: 2 liters) which has been initially charged with n-butanol and is brought to boiling for the reaction with stirring. The top of the column is connected to a reservoir vessel via a feed and an HPLC pump. Also present at the top of the column is an outlet for the components which can be distilled off during the reactive distillation, which is connected to a condenser and a phase separation vessel, and also a reflux for liquid condensate recovered.

To perform the reactive distillation, butanol steam is introduced from the stirred vessel, which is initially charged with pure n-butanol (1 liter) at the start, into the column and the column is operated in total reflux. As soon as the temperature profile (BuOH boiling point in the column) is stationary in the column, an aqueous solution of 558.86 g of diammonium succinate (DAS, DAS concentration=24%), admixed with 3.3 g of para-toluenesulfonic acid, is metered in by means of the HPLC pump at standard pressure and at the top of the bubble-cap tray column at a temperature between 90 (at the top of the column) to 118° C. (in the bottom, pure butanol at the start) and a feed rate of 0.2-0.7 ml/min.

During the reaction, the dibutyl succinate formed (DBS: b.p.=278° C. at standard pressure) becomes enriched in the bottom of the stirred vessel (together with butanol). During the synthesis, the internal temperature in the stirred vessel rises from 118.3° C. to 128.8° C. The water/n-butanol azeotrope and $NH_3$ are distilled off via the top and partly condensed. The uncondensed constituents (presumably $NH_3$ in particular) can leave the apparatus in a branch stream as waste air. In a phase separation vessel, the condensate is separated into a butanol phase and a water phase. The butanol phase is recycled via the condenser reflux into the column at the top.

Experimental Result:
DAS used: 558.86 g
p-Toluenesulfonic acid: 3.3 g
Yield (by GC analysis):
  Dibutyl succinate 96.5%,
  Succinic anhydride 0.3%,
  Amido butyl ester 0.1%
  Succinimide <<0.1%
Total nitrogen content 120 ppm.

The esterification effluent was filtered (succinic acid and pTsOH are precipitated out) and can then be hydrogenated further directly without further distillative purification.

Example 2

Catalytic Hydrogenation of Dibutyl Succinate to THF

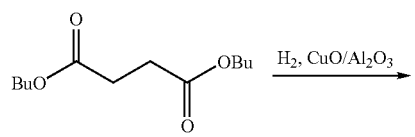

-continued

+ BuOH + $H_2O$

For the continuous hydrogenation (in the gas phase), the pressure apparatus consists of an evaporator (T=250° C.), a reactor, a condenser, a hydrogen feed, an offgas line and a compressor. The pressure in the apparatus is kept constant at 13 bar. The dibutyl succinate is evaporated and mixed with fresh hydrogen and cycle gas (mol(DBS):mol($H_2$)=1:1000). The mixture of hydrogen and ester passes into a reactor (24° C.) filled with catalyst (120 ml of $CuO/Al_2O_3$). The products are condensed in the condenser.

Experimental conditions: T(evaporator)=250° C., T(reactor)=240° C., pressure 13 bar, hourly space velocity=0.1 $kg_{ester}/l_{cat}$.h, molar reactant:$H_2$ ratio=1:1000

Yield (by GC analysis; full conversion of dibutyl succinate):
Dibutyl ester used: 2825 g
  THF=69.0%,
  BDO=0.0%,
  GBL=0.0%.

Other by-products are small amounts of butanol and dibutyl ether; loss of THF owing to stripping ($N_2$).

Total nitrogen content of the product: 110 ppm

Reference Example 1

Experiments on the Direct Catalytic Hydrogenation of Succinic Salts to THF

For comparative purposes, various salts of succinic acid were subjected to a homogeneous or heterogeneous hydrogenation. Either no reaction (disodium salt) or the formation of various hydrogenation products, such as BDO, GBL or pyrrolidone, is observed, but not the formation of the desired THF product.

| | | Product yields | | | |
|---|---|---|---|---|---|
| Substrate | Catalyst[a] | Butanediol (BDO) | γ-Butyrolactone (GBL) | THF | Pyrrolidone |
| disodium succinate | Ru/Triphos | | no reaction | | |
| | Sn/Pt | | no reaction | | |
| monosodium succinate | Ru/Triphos | 21.3%[b] | 3.3%[b] | — | — |
| | Sn/Pt | 10%[b] | 26.2%[b] | — | — |

-continued

| | | Product yields | | | |
|---|---|---|---|---|---|
| Substrate | Catalyst[a] | Butanediol (BDO) HO~~~OH | γ-Butyrolactone (GBL) | THF | Pyrrolidone |
| NH$_4^+$ $^-$O-CO-CH$_2$-CH$_2$-CO-O$^-$ NH$_4^+$ | Ru/Triphos | 8.6% | 3.7% | — | 4.2% |
| | Sn/Pt | — | 2.5% | — | 4.8% |

[a]Homogeneous hydrogenation conditions: Ru(acac)$_3$/Triphos, 150° C., 150 bar H$_2$, 24 h. Heterogeneous hydrogenation conditions: 3% Sn/7% Pt on C, 120° C., 200 bar H$_2$, 24 h.
[b]The monosodium salt can be regarded as a 50:50 mixture of diacid and disodium salt. Only the diacid could in butanediol BDO and GBL. No conversion of a sodium carboxylate was observed.

Reference Example 2

Preliminary Experiments on the Direct Esterification of Various Dicarboxylic Salts with Butanol Various alkali metal and alkaline earth metal salts of succinic acid and the diammonium salt of fumaric acid were esterified with butanol in a stirred flask (10 g of salt+1 g of pTsOH in BuOH, reflux for 96 h). The experimental results are compiled in the table below.

The inventive result of the conversion of diammonium succinate is also listed once again for comparison.

It is observed that, surprisingly, none of the succinic salts tested additionally is converted to the desired diester. The ammonium salt of fumaric acid was thus esterifiable with a lower yield than the corresponding succinic salt.

| | | Product yield | | | |
|---|---|---|---|---|---|
| Substrate | Catalyst[a] | BuO-CO-CH$_2$-CH$_2$-CO-OBu | BuO-CO-CH$_2$-CH$_2$-CO-OH | BuO-CO-CH$_2$-CH$_2$-CO-NH$_2$ | Other by-products[b] |
| Na$^+$ $^-$O-CO-CH$_2$-CH$_2$-CO-O$^-$ Na$^+$ | 0.5% pTsOH | no reaction | | | |
| $^-$O-CO-CH$_2$-CH$_2$-CO-O$^-$ Mg$^{++}$ | 0.5% pTsOH | no reaction | | | |
| HO-CO-CH$_2$-CH$_2$-CO-O$^-$ Na$^+$ | 0.5% pTsOH | Traces[c] | Traces[c] | — | — |
| NH$_4^+$ $^-$O-CO-CH=CH-CO-O$^-$ NH$_4^+$ | 10% pTsOH | 76%[d] | — | — | — |

| Substrate | Catalyst[a] | Product yield: BuO-succinate-OBu | BuO-succinate-OH | BuO-succinate-NH2 | Other by-products[b] |
|---|---|---|---|---|---|
| NH4+ -O-succinate-O- NH4+ | 0.5% pTsOH | 97% | — | 140 ppm[e] | — |

[a] p-TsOH: para-toluenesulfonic acid
[b] All products observed in the GC were identified by GC-MS analysis.
[c] The salt was insoluble in n-butanol; therefore, only the solution containing mono- and dibutyl ester could be analyzed in the GC. The monosodium salt can be considered as a 50:50 mixture of diacid and disodium salt. Only the diacid is esterifiable. No reaction of a sodium carboxylate was detected.
[d] The aim of this experiment was to check whether the fumaric salt can be converted to the dibutyl ester. An insoluble solid was observed (unconverted fumaric salt).
[e] Elemental analysis

Reference Example 3

Preparation of Dibutyl Succinate in a Flask

For the esterification reaction, a three-neck flask (500 ml) with a water separator is used, in which n-butanol, 52 g of diammonium succinate and 0.45 g of para-toluenesulfonic acid are initially charged. The mixture is brought to boiling with stirring. During the reaction, the dibutyl succinate formed is enriched in the flask (together with butanol). The water/n-butanol azeotrope and $NH_3$ are distilled off via the top and condensed in the water separator. The condensate is separated into a butanol phase and a water phase. The butanol phase is recycled into the flask. The reaction ran for a total of 240 hours.
Experimental Result:
DAS used: 52 g (342 mmol)
p-Toluenesulfonic acid: 0.45 g (0.79 mmol)
n-Butanol: approx. 200 g
Run time: 240 hours
Yield (by GC analysis):
dibutyl succinate 95.9%,
monobutyl succinate 1.5%,
succinic anhydride 0.04%,
amido butyl ester 1.0%
succinimide 0.6%

It is observed that, owing to the different process regime, a significantly higher level of undesired nitrogen-containing by-products (1.6% in total) is formed, whereas less than 0.2% of such compounds are formed in accordance with the invention (example 1).

REFERENCE NUMERAL LIST

| | |
|---|---|
| 1 | Reservoir vessel (ammonium salt solution) |
| 2 | Stirred vessel (initial alcohol charge, evaporator, bottom) |
| 3 | Bubble-cap tray column |
| 4 | Bubble-cap tray |
| 5 | Lower end of the column |
| 6 | Top of the column |
| 7 | Initial charge inlet |
| 8 | Column-stirred vessel connection |
| 9 | Stirrer |
| 10 | Azeotrope outlet (vapor line) |
| 11 | Condenser |
| 12 | Outlet |
| 13 | Phase separation vessel |
| 14 | Offgas line |
| 15 | Water phase outlet |
| 16 | Organic phase recycling |
| 101 | Reservoir vessel (ammonium salt solution) |
| 102 | Alcohol reservoir vessel |
| 103 | Ammonium salt solution inlet (from precursor) |
| 104 | Alcohol inlet |
| 105 | Ammonium salt solution inlet |
| 106 | Alcohol inlet |
| 107 | Column |
| 108 | Evaporator |
| 109 | Draw line for residues (optional) |
| 110a | Bottom draw: ester (alcohol) mixture |
| 110b | Bottoms recycling |
| 110c | Column inlet |
| 111a | Organic phase recycling |
| 111b | Aqueous phase recycling (optional) |
| 112 | Phase separation vessel |
| 113 | Condenser |
| 114 | Offgas line |
| 114a | Outlet |
| 115 | Water phase outlet |
| 116 | Azeotrope outlet (vapor line) |
| 117 | Top of the column |
| 118 | Bottom |
| 119 | Internals (such as bubble-cap trays) |

The invention claimed is:

1. A process for preparing a polycarboxylic acid ester via reactive distillation comprising (1) esterifying an ammonium salt of at least one polycarboxylic acid by contacting an initial charge comprising an aqueous solution of said ammonium salt of at least one polycarboxylic acid with at least one alkanol in a distillation column to form a polycarboxylic acid ester and (2) removing ammonia and water obtained from said esterification by distillation, wherein said aqueous solution of an ammonium salt of at least one polycarboxylic acid and said at least one alkanol are fed to said distillation column in at least two separate reactant streams such that said at least one alkanol is fed in at least one theoretical plate or at least one tray below the feed of said aqueous solution of an ammonium salt of at least one polycarboxylic acid.

2. The process of claim 1, wherein said polycarboxylic acid ester is enriched in the bottom of said distillation column.

3. The process of claim 1, wherein said ammonium salt of at least one polycarboxylic acid is selected from the group consisting of unsaturated $C_3$-$C_{20}$-polycarboxylic acids and saturated $C_3$-$C_{20}$-polycarboxylic acids.

4. The process of claim 1, wherein said at least one alkanol is selected from the group consisting of straight-chain $C_1$-$C_6$-monoalkanols or branched $C_1$-$C_6$-monoalkanols.

5. The process of claim 1, wherein the polycarboxylic acid of said ammonium salt of at least one polycarboxylic acid is partly or fully neutralized with ammonia.

6. The process of claim 1, wherein said aqueous solution of said ammonium salt of at least one polycarboxylic acid is fed in the upper half of said distillation column.

7. The process of claim 1, wherein said released ammonia and water, and optionally alkanol, are distilled via the top of said distillation column.

8. The process of claim 7, wherein an alkanol/water azeotrope and ammonia are distilled off and condensed, and said alkanol is removed from the condensate and recycled into the reaction.

9. The process of claim 7, wherein an alkanol/water heteroazeotrope and ammonia are distilled off and condensed, and said alkanol is removed from the condensate and recycled into the reaction.

10. The process of claim 1, wherein said esterification is carried out in the presence of an esterification catalyst.

11. The process of claim 10, wherein said esterification catalyst is homogeneous or heterogeneous.

12. The process of claim 11, wherein said heterogeneous esterification catalyst is an acidic ion exchange catalyst.

13. The process of claim 11, wherein said heterogeneous esterification catalyst is fixed on or in the internals of said distillation column.

14. The process of claim 11, wherein said homogeneous esterification catalyst is added to said aqueous solution of said ammonium salt of at least one polycarboxylic acid.

15. The process of claim 14, wherein said homogeneous esterification catalyst is p-toluenesulfonic acid or methanesulfonic acid.

16. The process of claim 1, wherein said ammonium salt of at least one polycarboxylic acid is diammonium succinate.

17. The process of claim 1, wherein said ammonium salt of at least one polycarboxylic acid is prepared chemically.

18. The process of claim 1, wherein said initial charge comprises an optionally prepurified and/or concentrated fermentation broth.

19. The process of claim 18, wherein said optionally prepurified and/or concentrated fermentation broth is derived from the cultivation of a microorganism which ferments pentoses and/or hexoses and/or polyols.

20. The process of claim 1, wherein said at least one alkanol is n-butanol.

21. The process of claim 20, wherein said polycarboxylic acid ester is di-n-butyl succinate.

22. The process of claim 1, wherein said reactive distillation is performed essentially without supply of inert gas into the distillation column.

23. The process of claim 1, wherein said at least one alkanol is fed in from 5 to 20 theoretical plates or trays below the feed of said aqueous solution of said ammonium salt of at least one polycarboxylic acid.

* * * * *